US010575479B2

(12) United States Patent
Scheurwater (10) Patent No.: US 10,575,479 B2
(45) Date of Patent: Mar. 3, 2020

(54) LACTUCA SATIVA WITH BREMIA LACTUCAE (DOWNY MILDEW) RESISTANCE

(71) Applicant: BEJO ZADEN BV, Warmenhuizen (NL)

(72) Inventor: Teunis Scheurwater, Nieuw-Lekkerland (NL)

(73) Assignee: Bejo Zaden BV, Warmenhuizen (NL)

(*) Notice: Subject to any disclaimer, the term of this patent is extended or adjusted under 35 U.S.C. 154(b) by 264 days.

(21) Appl. No.: 14/771,383

(22) PCT Filed: Feb. 27, 2014

(86) PCT No.: PCT/EP2014/053881
§ 371 (c)(1),
(2) Date: Aug. 28, 2015

(87) PCT Pub. No.: WO2014/131857
PCT Pub. Date: Sep. 4, 2014

(65) Prior Publication Data
US 2016/0007552 A1 Jan. 14, 2016

(30) Foreign Application Priority Data
Feb. 28, 2013 (NL) .................................... 1040073

(51) Int. Cl.
*A01H 1/04* (2006.01)
*A01H 6/14* (2018.01)
*A01H 5/12* (2018.01)

(52) U.S. Cl.
CPC ................. *A01H 1/04* (2013.01); *A01H 5/12* (2013.01); *A01H 6/1472* (2018.05)

(58) Field of Classification Search
None
See application file for complete search history.

(56) References Cited

U.S. PATENT DOCUMENTS

| 5,378,619 | A | 1/1995 | Rogers | |
|---|---|---|---|---|
| 5,563,055 | A | 10/1996 | Townsend et al. | |
| 7,790,962 | B2* | 9/2010 | Moor | A01H 6/1472 800/305 |
| 2010/0306872 | A1* | 12/2010 | Moor | A01H 5/12 800/265 |
| 2012/0328764 | A1* | 12/2012 | Moor | A01H 5/12 426/615 |
| 2013/0108771 | A1* | 5/2013 | Crins | A01H 5/12 426/615 |

FOREIGN PATENT DOCUMENTS

| EP | 0629343 | A2 | 12/1994 |
|---|---|---|---|
| WO | 1990001069 | A1 | 2/1990 |
| WO | 2000063432 | A1 | 10/2000 |
| WO | 2009111627 | A1 | 9/2009 |
| WO | 2011003783 | A1 | 1/2011 |

OTHER PUBLICATIONS

Simko et al. Indentification of QTLs conferring resistance to downy mildew in legacy cultivars of lettuce. Scientific Reports. 2013. pp. 1-10.*
Kuang et al. Evolution and genetic population structure of prickly lettuce (*Lactuca serriola*) and its RGC2 gene cluster. Genetics Society of America. 2008. 178: 1547-1558.*
Kesseli et al. Analysis of a detailed genetic linkage map of *Lactuca sativa* (Lettuce) constructed from RFLP and RPD markers. Genetics Society of America. 1994. 136: 1435-1446.*
GenBank Accession No. JO036145. TSA: Lactuca serriola Serrassy_T_P2_15279 mRNA sequence. published Jan. 14, 2013. pp. 1-2.*
Matvienko et al. TSA: Lactuca sativa CLC_LTR_V1A_41293 mRNA sequence. GenBank Accession No. JI61440. published Apr. 25, 2011. pp. 1.*
Lebeda et al. Race-specific resistance genes to Bremia lactucae Regel in new Czechoslovak lettuce cultivars and location of resistance in a Lactuca serriola x Lactuca sativa hybrid. Arch. Phytopathol. 1991. 27: 65-72.*
Department of Environment, Food and Rural Affairs. Development of disease control strategies for organically grown field vegetables (DOVE). CSG 15. Sep. 2001. pp. 1-23.*
A. Lebeda et al., "Phenotypic and histological expression of different genetic backgrounds in interactions between lettuce, wild *Lactuca* spp., L. *sativa* x L. *serriola* hybrids and Bremia lactucae", European Journal of Plant Pathology, vol. 115, No. 4, DOI: 10.1007/s10658-006-9034-3, 2006, pp. 431-441.
A. Lebeda, "Response of Lettuce Cultivars Carrying the Resistance Gene Dm11 to Isolates of Bremia lactucae from Lactuca serriola", Plant Breeding, vol. 102, Issue 4, DOI: 10.1111/j.1439-0523.1989. tb01261.x, May 1989, pp. 311-316.
A. Lebeda et al., "Wild Lactuca germplasm for lettuce breeding: current status, gaps and challenges", Euphytica, vol. 170, No. 1; DOI: 10.1007/s10681-009-9914-7, Mar. 17, 2009, pp. 15-34.
A. Schaffner et al., "Maize rbcS promoter activity depends on sequence elements not found in dicot rbcS promoters", Plant Cell., vol. 3, No. 9, Sep. 1991, pp. 997-1012.
B. Farrara et al., "Genetic analysis of factors for resistance to downy mildew (*Bremia lactucae*) in species of lettuce (*Lactuca sativa* and L. *serriola*)", Department of Vegetable Crops, University of California, Davis, California 95616, USA, Plant Pathology (Impact Factor: 2.12), vol. 36, No. 4, DOI: 10.1111/j.1365-3059.1987. tb02267.x, 1987, pp. 499-514.
B. Siebertz et al., "cis-Analysis of the Wound-Inducible Promoter wun1 in Transgenic Tobacco Plants and Histochemical Localization of its Expression", The Plant Cell, vol. 1, American Society of Plant Physiologists, Oct. 1989, pp. 961-968.

(Continued)

*Primary Examiner* — Ashley K Buran
(74) *Attorney, Agent, or Firm* — The Webb Law Firm (57) ABSTRACT

The current invention concerns a *Lactuca sativa* plant resistant to *Bremia lactucae*, characterized in that the *Bremia* resistance locus is linked to a genetic determinant and obtainable from the genome of a wild *Lactuca* plant, preferably from the genome of *Lactuca serriola*. The current invention also relates to seed and other plant material obtainable from this plant as well as to a method for obtaining said plant.

17 Claims, 2 Drawing Sheets

Specification includes a Sequence Listing.

(56) References Cited

OTHER PUBLICATIONS

C. Kuhlemeier et al., "The Pea rbcS-3A Promoter Mediates Light Responsiveness but not Organ Specificity", Plant Cell., vol. 1, No. 4, Apr. 1989, pp. 471-478.

D. Nickerson et al., "Automated DNA diagnostics using an ELISA-based oligonucleotide ligation assay", Proc Natl Acad Sci U S A., vol. 87 No. 22, Genetics,, Nov. 1990, pp. 8923-8927.

D. Wu et al., "The ligation amplification reaction (LAR)—amplification of specific DNA sequences using sequential rounds of template-dependent ligation", Genomics, vol. 4, 1989, pp. 560-569.

F. Barany, "Genetic disease detection and DNA amplification using cloned thermostable ligase", Proc Natl Acad Sci U S A., vol. 88 No. 1, Jan. 1, 1991, pp. 189-193.

H. Fromm et al., "An octopine synthase enhancer element directs tissue-specific expression and binds ASF-1, a factor from tobacco nuclear extracts", Plant Cell., vol. 1, No. 10, Oct. 1989, pp. 977-984.

H. Klee et al., "Vectors for Transformation of Higher Plants", Nature Biotechnology, vol. 3, doi:10.1038/nbt0785-637, Jul. 1985, pp. 637-642.

H. Uchimiya et al., "Expression of a foreign gene in callus derived from DNA-treated protoplasts of rice (*Oryza sativa* L.)", Molecular and General Genetics MGG, vol. 204, No. 2, 1986, pp. 204-207.

I. Curtis, "Lettuce (*Lactuca sativa* L.)", Methods Mol Biol., vol. 343, 2006, pp. 449-458.

I. Potrykus et al., "Direct gene transfer to cells of a graminaceous monocot", Molecular and General Genetics MGG, vol. 199, No. 2, May 1985, pp. 183-188.

J. Callis et al., "Heat Inducible Expression of a Chimeric Maize hsp70CAT Gene in Maize Protoplasts", Plant Physiol., vol. 88, No. 4, Dec. 1988, pp. 965-968.

J. Odell et al., "Identification of DNA sequences required for activity of the cauliflower mosaic virus 35S promoter", Nature, vol. 313, doi:10.1038/313810a0, Feb. 28, 1985, pp. 810-812.

J. Schernthaner et al., "Endosperm-specific activity of a zein gene promoter in transgenic tobacco plants", EMBO J., vol. 7, No. 5, May 1988, pp. 1249-1255.

J. Simpson et al., "Light-inducible and tissue-specific expression of a chimaeric gene under control of the 5'-flanking sequence of a pea chlorophyll a/b-binding protein gene", The EMBO Journal, vol. 4, No. 11, 1985, pp. 2723-2729.

K. Mullis et al., "Specific enzymatic amplification of DNA in vitro: the polymerase chain reaction", Cold Spring Harb Symp Quant Biol., vol. 51, Pt. 1, 1986, pp. 263-273.

M. Bustos et al., "Regulation of beta-glucuronidase expression in transgenic tobacco plants by an A/T-rich, cis-acting sequence found upstream of a French bean beta-phaseolin gene", Plant Cell., vol. 1 No. 9, Sep. 1989, pp. 839-853.

M. Fromm et al., "Stable transformation of maize after gene transfer by electroporation", Nature, vol. 319, No. 6056, Feb. 27, 1986, pp. 791-793.

P. Choi et al.,"Genetic transformation and plant regeneration of watermelon using Agrobacterium tumefaciens", Plant Cell Rep., vol. 13, No. 6, doi: 10.1007/BF00232634., 1994, pp. 344-348.

P. Ellul et al., "The expression of the *Saccharomyces cerevisiae* HAL1 gene increases salt tolerance in transgenic watermelon [Citrullus lanatus (Thunb.) Matsun. & Nakai.]", Theor Appl Genet., vol. 107, No. 3, May 29, 2003, pp. 462-469.

R. Dekeyser et al., "Evaluation of Selectable Markers for Rice Transformation", Plant Physiol., vol. 90, No. 1, May 1989, pp. 217-223.

R. Fraley et al., "The SEV System: A New Disarmed Ti Plasmid Vector System for Plant Transformation", Nature Biotechnology, vol. 3, doi:10.1038/nbt0785-629, Jul. 1985, pp. 629-635.

R. Michelmore et al., "Identification of markers linked to disease-resistance genes by bulked segregant analysis: a rapid method to detect markers in specific genomic regions by using segregating populations", Proc. Natl. Acad. Sci. USA, vol. 88, No. 21, Genetics, doi: 10.1073/pnas.88.21.9828, Nov. 1991, pp. 9828-9832.

R. Terada et al., "Expression of CaMV35S-GUS gene in transgenic rice plants", Molecular and General Genetics MGG, vol. 220, No. 3, Feb. 1990, pp. 389-392.

S. Omirulleh et al., "Activity of a chimeric promoter with the doubled CaMV 35S enhancer element in protoplast-derived cells and transgenic plants in maize", Plant Mol Biol., vol. 21, No. 3, Feb. 1993, pp. 415-428.

S. Rosahl et al., "Expression of a tuber-specific storage protein in transgenic tobacco plants: demonstration of an esterase activity", EMBO J., vol. 6, No. 5, May 1987, pp. 1155-1159.

U. Landegren et al., "A ligase-mediated gene detection technique", Science, vol. 241 No. 4869, Aug. 26, 1988, pp. 1077-1080.

W. Marcotte Jr. et al., "Abscisic acid-responsive sequences from the em gene of wheat", Plant Cell., vol. 1, No. 10, Oct. 1989, pp. 969-976.

W. Marcotte Jr., "Regulation of a wheat promoter by abscisic acid in rice protoplasts", Nature, vol. 335, doi:10.1038/335454a0, Sep. 29, 1988, pp. 454-457.

\* cited by examiner

LACTUCA SATIVA WITH BREMIA LACTUCAE (DOWNY MILDEW) RESISTANCE

This application is a national stage application under 35 U.S.C. § 371 of International Application No. PCT/EP2014/053881, filed Feb. 27, 2014, entitled "*LACTUCA SATIVA* WITH *BREMIA LACTUCAE* (DOWNY MILDEW) RESISTANCE," which claims priority to Netherlands Patent Application No. NL1040073, filed Feb. 28, 2013, the contents of all of which are hereby incorporated herein in their entirety by reference for all purposes.

SEQUENCE LISTING

A sequence listing submitted in computer readable format is hereby incorporated by reference. The computer readable file is named 20140227_ASEM-004-NL-WO_final_ST25.txt, was created on Feb. 27, 2014, and contains 1 kilobytes.

TECHNICAL FIELD

The present invention relates to the field of plant breeding and, more specifically, to the development of downy mildew-resistant lettuce having elite agronomic traits.

On Nov. 13, 2012, seeds of AS-002 deposited under the Budapest Treaty according to 37 CFR 1.803(a)(1), with an International Depositary Authority (IDA). The deposit was made with the NCIMB Ltd. in Aberdeen, Scotland, and received Accession No. NCIMB 42082. The deposited seeds will be available during the pendency of the application to the Commissioner of Patents and Trademarks and persons determined by the Commissioner to be entitled thereto upon request. Upon issue of claims, Applicant will make the deposited seeds available to the public for the enforceable life of the patent.

BACKGROUND

Cultivated lettuce, *Lactuca sativa*, is a temperate annual or biennial plant most often grown as a leaf vegetable. Lettuce belongs to the aster or sunflower family Asteraceae. Other members of this family include endive, chicory, artichoke, sunflower and safflower. It is closely related to common wild lettuce or prickly lettuce (*L. serriola*) and less closely related to two other wild lettuces (*L. saligna* and *L. virosa*). Cultivated lettuce and sunflower the genetically characterized members of this family. Four principal types of cultivated lettuce include crisphead (mostly iceberg), romaine (cos), leaf and butterhead. Each of these basic groups is comprised of numerous cultivars, each characterized by its own particular morphology, cultural adaptations, and diseases resistance. Lettuce cultivars can display a number of idseases caused by Downy Mildew, *Sclerotinia* Rot, *Botrytis* Rot, Corky Root Rot, Bacterial leafspot of lettuce, caused by *Xanthomonas campestris* pv. vitians, and lettuce mosaic virus, among others. Among the most important fungal diseases of lettuce is Downy Mildew, caused by *Bremia lactucae*. *L. saligna* displays quantitative resistance to *Bremia lactucae* such that it is generally considered to be a non-host plant of this oomycete, and has been studied as a potential source of genetic resistance to this disease. There remains a need in the art to provide plants which are less or not susceptible to the various known *Bremia lactucae* races.

SUMMARY OF THE INVENTION

The current invention aims to provide at least one *Lactuca sativa* plant which is resistant to a broad spectrum of *Bremia lactucae* races, preferably to at least *Bremia lactucae* races Bl:1 to Bl:28.

The present invention therefore provides, but is not limited to:

1. *Lactuca sativa* plant resistant to *Bremia lactucae*, characterized in that the *Bremia* resistance locus is linked to a genetic determinant and obtainable from the genome of a wild *Lactuca* plant, preferably from the genome of *Lactuca serriola*.

2. The plant according to the preceding embodiment, characterized in that said *Bremia lactucae* resistance locus is a broad spectrum *Bremia lactucae* resistance locus.

3. The plant according to any of the preceding embodiments, characterized in that said *Bremia lactucae* resistance locus provides resistance to *Bremia lactucae* races Bl:1 to Bl:28.

4. The plant according to any of the preceding embodiments, characterized in that said plant is obtainable through crossing of *Lactuca sativa* AS-002, of which representative seed has been deposited at the NCIMB Ltd. Under Accession N° NCIMB 42082, and any other susceptible *Lactuca sativa* plant, followed by selecting of plants that display the *Bremia lactucae* resistance.

5. The plant according to any of the preceding embodiments, characterized in that said *Bremia* resistance locus co-segregates with a sequence which has at least 90% homology, more preferably 95% homology with a sequence chosen from SEQ ID No. 1 or SEQ ID No. 2.

6. Seed of a
   a. homozygous plant according to any of the preceding embodiments; or
   b. *Lactuca sativa* plant as claimed in any of the preceding embodiments, comprising the genetic determinant contributing to resistance to *Bremia lactucae*; or
   c. a hybrid plant; or
   d. a plant with the genetic background of NCIMB 42082 characterized in that said genetic determinant contributing to *Bremia lactucae* resistance provides resistance to at least *Bremia lactucae* races Bl:1 to Bl:28.

7. A method for introducing at least one allele associated with resistance to *Bremia lactucae* at a R gene R-genelocus contributing to resistance to *Bremia* into a *Lactuca sativa* plant lacking said allele comprising:
   e. obtaining a first *Lactuca sativa* plant according to any one of the preceding embodiments;
   f. crossing said first *Lactuca sativa* plant with a second *Lactuca sativa* plant, wherein said second *Lactuca sativa* plant lacks said allele; and
   g. identifying a plant resulting from the cross exhibiting increased resistance to *Bremia lactucae* and comprising at least one determinant marker determinant co-segregating with said *Bremia* resistance; and
   h. optionally, isolating said plant and
   i. optionally, back-crossing said plant with the first or second *Lactuca sativa* plant.

8. Method according to the previous embodiment, characterized in that said determinant marker has at least 90% homology, more preferably 95% homology with a sequence chosen from SEQ ID No. 1 or SEQ ID No. 2.

8. A method of obtaining a *Lactuca sativa* plant resistant against *Bremia lactucae*, comprising:

j. obtaining a F1-hybrid by crossing a *Lactuca serriola* plant with a *Lactuca sativa* plant, which is sensitive to infestation with *Bremia lactucae*;

k. backcrossing the F1-hybrid with said *Lactuca sativa* plant; and l. identifying a plant resulting from the cross exhibiting resistance to *Bremia lactucae* and comprising at least one marker determinant co-segregating with said *Bremia* resistance, and m. optionally, growing said plant.

9. Use of a seed according to the preceding embodiments for growing a *Lactuca sativa* plant resistant to *Bremia lactucae*.

10. Plant material obtainable from a plant according to any of the preceding embodiments, including but without being limited thereto, leaves, stems, roots, flowers or flower parts, fruits, pollen, egg cells, zygotes, seeds, cuttings, cell or tissue cultures, or any other part or product of the plant which still exhibits the *Bremia* resistance, particularly when grown into a plant.

11. Plant parts of a plant according to any of the preceding embodiments including, but without being limited thereto, plant seed, plant organs such as, for example, a root, stem, leaf, flower bud, or embryo, ovules, pollen microspores, plant cells, plant tissue, plant cells cultures such as, for example, protoplasts, cell culture cells, cells in plant tissues, pollen, pollen tubes, ovules, embryo sacs, zygotes and embryos at various stages of development, which still exhibits the *Bremia* resistance, particularly when grown into a plant.

12. Head or leaves of cultivated lettuce plants of any of the preceding embodiments.

13. A marker determinant linked to and co-segregating with a *Bremia lactucae* resistance locus in a *Lactuca sativa* plant according to preceding embodiments.

14. Marker according to the previous embodiment, characterized in that said marker has at least 90% homology, more preferably 95% homology with a sequence chosen from SEQ ID No. 1 or SEQ ID No. 2.

15. A *Bremia lactucae* resistance locus obtainable from the genome of a wild *Lactuca* plant, by preference a *Lactuca serriola*, characterized in that said resistance locus is a broad spectrum locus offering resistance to at least *Bremia lactucae* races Bl:1 to Bl:28.

16. *Bremia lactucae* resistance locus according to the previous embodiment, characterized in that said resistance locus co-segregates with a sequence having at least 90% homology, more preferably 95% homology with a sequence chosen from SEQ ID No. 1 or SEQ ID No. 2.

DETAILED DESCRIPTION OF THE INVENTION

The present invention relates to novel plants resistant to *Bremia lactucae*, preferably to *Bremia lactucae* races Bl:1 to Bl:28, and to seeds of said plants. The present invention also relates to methods of making such plants and for producing seeds thereof. The invention further relates to markers and the use of the latter in marker assisted breeding and in the identification of the *Bremia* resistance trait.

Definitions

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

A cultivated "*Lactuca sativa*" plant is understood within the scope of the invention to refer to a plant that is no longer in the natural state but has been developed by human care and for human use and/or consumption.

An "allele" is understood within the scope of the invention to refer to alternative or variant forms of various genetic units identical or associated with different forms of a gene or of any kind of identifiable genetic element, which are alternative in inheritance because they are situated at the same locus in homologous chromosomes. Such alternative or variant forms may be the result of single nucleotide polymorphism, insertions, inversions, translocations or deletions, or the consequence of gene regulation caused by, for example, by chemical or structural modification, transcription regulation or post-translational modification/regulation. In a diploid cell or organism, the two alleles of a given gene or genetic element typically occupy corresponding loci on a pair of homologous chromosomes. Alleles determine distinct traits that can be passed on from parents to offspring. The process by which alleles are transmitted was discovered by Gregor Mendel and formulated in what is known as Mendel's law of segregation.

An allele associated with an R-gene may comprise alternative or variant forms of various genetic units including those that are identical or associated with a single gene or multiple genes or their products or even a gene disrupting or controlled by a genetic factor contributing to the phenotype represented by the locus.

As used herein, the term "marker determinant" refers to an alternative or variant form of a genetic unit as defined herein above, when used as a marker to locate genetic loci containing alleles on a chromosome that contribute to variability of phenotypic traits.

As used herein, the term "breeding", and grammatical variants thereof, refer to any process that generates a progeny individual. Breedings can be sexual or asexual, or any combination thereof. Exemplary non-limiting types of breedings include crossings, settings, doubled haploid derivative generation, and combinations thereof.

As used herein, the phrase "established breeding population" refers to a collection of potential breeding partners produced by and/or used as parents in a breeding program; e.g., a commercial breeding program. The members of the established breeding population are typically well-characterized genetically and/or phenotypically. For example, several phenotypic traits of interest might have been evaluated, e.g., under different environmental conditions, at multiple locations, and/or at different times. Alternatively or in addition, one or more genetic loci associated with expression of the phenotypic traits might have been identified and one or more of the members of the breeding population might have been genotyped with respect to the one or more genetic loci as well as with respect to one or more genetic markers that are associated with the one or more genetic loci.

As used herein, the phrase "diploid individual" refers to an individual that has two sets of chromosomes, typically one from each of its two parents. However, it is understood that in some embodiments a diploid individual can receive its "maternal" and "paternal" sets of chromosomes from the same single organism, such as when a plant is selfed to produce a subsequent generation of plants.

"Homozygous" is understood within the scope of the invention to refer to like alleles at one or more corresponding loci on homologous chromosome.

"Heterozygous" is understood within the scope of the invention to refer to unlike alleles at one or more corresponding loci on homologous chromosomes.

"Backcrossing" is understood within the scope of the invention to refer to a process in which a hybrid progeny is repeatedly crossed back to one of the parents. Different recurrent parents may be used in subsequent backcrosses.

"Locus" is understood within the scope of the invention to refer to a region on a chromosome.

As used herein, "marker focus" refers to a region on a chromosome, which comprises a nucleotide or a polynucleotide sequence that is present in an individual's genome and that is associated with one or more loci of interest, which may which comprise a gene or any other genetic element or factor contributing to a trait. "Marker locus" also refers to a region on a chromosome, which comprises a polynucleotide sequence complementary to a genomic sequence, such as a sequence of a nucleic acid used as probes.

"Genetic linkage" is understood within the scope of the invention to refer to an association of characters in inheritance due to location of genes in proximity on the same chromosome, measured by percent recombination between loci (centi-Morgan, cM).

For the purpose of the present invention, the term "co-segregation" refers to the fact that the allele for the trait and the allele(s) for the marker(s) tend to be transmitted together because they are physically close together on the same chromosome (reduced recombination between them because of their physical proximity) resulting in a non-random association of their alleles as a result of their proximity on the same chromosome. "Co-segregation" also refers to the presence of two or more traits within a single plant of which at least one is known to be genetic and which cannot be readily explained by chance.

As used herein, the term "genetic architecture at the R-gene locus" refers to a genomic region which is statistically correlated to the phenotypic trait of interest and represents the underlying genetic basis of the phenotypic trait of interest.

As used heroin, the phrases "sexually crossed" and "sexual reproduction" in the context of the presently disclosed subject matter refers to the fusion of gametes to produce progeny (e.g., by fertilization, such as to produce seed by pollination in plants). A asexual cross" or "cross-fertilization" is in some embodiments fertilization of one individual by another (e.g., cross-pollination in plants). The term "selling" refers in some embodiments to the production of seed by self-fertilization or self-pollination; i.e., pollen and ovule are from the same plant.

As used herein, the phrase "genetic marker" refers to a feature of an individual's genome (e.g., a nucleotide or a polynucleotide sequence that is present in an individual's genome) that is associated with one or more loci of interest. In some embodiments, a genetic marker is polymorphic in a population of interest, or the locus occupied by the polymorphism, depending on contest. Genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DART) markers, and amplified fragment length polymorphism (AFLPs), among many other examples. Genetic markers can, for example, be used to locate genetic loci containing alleles on a chromosome that contribute to variability of phenotypic traits. The phrase "genetic marker" can also refer to a polynucleotide sequence complementary to a genomic sequence, such as a sequence of nuclei acids used as probes.

A genetic marker can be physically located in a position on a chromosome that is within or outside of the genetic locus with which it is associated (i.e., is intragenic or extragenic, respectively). Stated another way, whereas genetic markers are typically employed when the location on a chromosome of the gene or of a functional mutation, e.g. within a control element outside of a gene, that corresponds to the locus of interest has not been identified and there is a non-zero rate of recombination between the genetic marker and the locus of interest, the presently disclosed subject matter can also employ genetic markers that are physically within the boundaries of a genetic locus (e.g., inside a genomic sequence that corresponds to a gene such as, but not limited to a polymorphism within an intron or an exon of a gene).

"Microsatellite or SSRs (Simple sequence repeats) Marker" is understood within the scope of the invention to refer to a type of genetic marker that consists of numerous repeats of short sequences of DNA bases, which are found at loci throughout the plant's genome and have a likelihood of being highly polymorphic.

As used herein, the term "genotype" refers to the genetic constitution of a cell or organism. An individual's "genotype for a set of genetic markers" includes the specific alleles, for one or more genetic marker loci, present in the individual's haplotype. As is known in the art, a genotype can relate to a single locus or to multiple loci, whether the loci are related or unrelated and/or are linked or unlinked. In some embodiments, an individual's genotype relates to one or more genes that are related in that the one or more of the genes are involved in the expression of a phenotype of interest (e.g., a quantitative or R-gene as defined herein). Thus, in some embodiment a genotypes comprises a summary of one or more alleles present within an individual at one or more genetic loci of a quantitative or R-gene. In some embodiments, a genotype is expressed in terms of a haplotype (defined herein below).

As used herein, the term "germplasm" refers to the totality of the genotypes of a population or other group of individuals (e.g., a species). The term "germplasm" can also refer to plant material; e.g., a group of plants that act as a repository for various alleles. The phrase "adapted germplasm" refers to plant materials of proven genetic superiority; e.g., for a given environment or geographical area, while the phrases "non-adapted germplasm," "raw germplasm," and "exotic germplasm" refer to plant material of unknown or unproven genetic value; e.g., for a given environment or geographical area; as such, the phrase "non-adapted germplasm" refers in some embodiments to plant materials that are not part of an established breeding population and that do not have a known relationship to a member of the established breeding population.

As used herein, the terms "hybrid", "hybrid plant," and "hybrid progeny" refers to an individual produced from genetically different parents (e.g., a genetically heterozygous or mostly heterozygous individual).

As used herein, the phrase "single cross F1 hybrid" refers to an F1 hybrid produced from a cross between two inbred lines.

As used herein, the phrase "inbred line" refers to a genetically homozygous or nearly homozygous population. An inbred line, for example, can be derived through several cycles of brother/sister breedings or of selfing or in dihaploid production. In some embodiments, inbred lines breed true for one or more phenotypic traits of interest. An "inbred", "inbred individual, or "inbred progeny" is an individual sampled from an inbred line.

As used herein, the term "double haploid (DH) line", refers to stable inbred lines issued from another culture. Some pollen grains (haploid) cultivated on specific medium and circumstances can develop plantlets containing n chromosomes. These plantlets are then "double" and contain 2n chromosomes. The progeny of these plantlets are named "double haploid" and are essentially not segregating any more (stable).

As used herein, the term "linkage", and grammatical variants thereof, refers to the tendency of alleles at different loci on the same chromosome to segregate together more often than would be expected by chance if their transmission were independent, in some embodiments as a consequence of their physical proximity.

As used herein, the phrase "nucleic acid" refers to any physical string of monomer units that can be corresponded to a string of nucleotides, including a polymer of nucleotides (e.g., a typical DNA, cDNA or RNA polymer), modified oligonucleotides (e.g., oligonucleotides comprising bases that are not typical to biological RNA or DNA, such as 2'-O-methylated oligonucleotides), and the like. In some embodiments, a nucleic acid can be single-stranded, double-stranded, multi-stranded, or combinations thereof. Unless otherwise indicated, a particular nucleic acid sequence of the presently disclosed subject matter optionally comprises or encodes complementary sequences, in addition to any sequence explicitly indicated.

As used herein, the phrase "phenotypic trait" refers to the appearance or other detectable characteristic of an individual, resulting from the interaction of its genome, proteome and/or metabolome with the environment.

As used herein, the phrase "resistance" refers to the ability of a plant to restrict the growth and development of a specified pathogen and/or the damage they cause when compared to susceptible plants under similar environmental conditions and pathogen pressure. Resistant plants may exhibit some disease symptoms or damage under pathogen pressure, e.g. fungal pathogen pressure such as *Bremia lactucae* pathogen pressure.

As used herein, the phrase "susceptibility" refers to the inability of a plant to adequately restrict the growth and development of a specified pathogen, e.g. fungal pathogen such as *Bremia lactucae*.

As used herein, the phrase "*Bremia* resistance" or "resistance to *Bremia* races" or "*Bremia* resistant plant" refers to the plants capability to resist colonization by the fungus *Bremia lactucae*, isolates Bl:1 to Bl:28 as characterized and classified according to SEXTET code by IBEB (International *Bremia* Evaluation Board).

Resistant plants will show no or very few neuroses with no or very sparse sporulation under the test conditions defined in Example 1 below.

As used herein, the term "plurality" refers to more than one. Thus, a "plurality of individuals" refers to at least two individuals, in some embodiments, the term plurality refers to more than half of the whole. For example, in some embodiments a "plurality of a population" refers to more than half the members of that population.

As used herein, the term "progeny" refers to the descendant(s) of a particular across. Typically, progeny result from breeding of two individuals, although some species (particularly some plants and hermaphroditic animals) can be selfed (i.e., the same plant acts as the donor of both male and female gametes). The descendant(s) can be, for example, of the F1, the F2, or any subsequent generation.

As used herein, the phrase "R-gene" refers to a phenotypic trait that is controlled by one or a few genes that exhibit major phenotypic effects. Because of this, R-genes are typically simply inherited. Examples in plants include, but are not limited to, flower color, fruit color, and several known disease resistances such as, for example, Fungus spot resistance.

"Marker-assisted selection." is understood within the scope of the invention to refer to e.g. the use of genetic markers to detect one or more nucleic acids from the plant, where the nucleic acid is associated with a desired trait to identify plants that carry genes for desirable (or undesirable) traits, so that those plants can be used (or avoided) in a selective breeding program.

"PCR (polymerase chain reaction)" is understood within the scope of the invention to refer to a method of producing relatively large amounts of specific regions of DNA or subset(s) of the genome, thereby making possible various analyses that are based on those regions.

"PCR primer" is understood within the scope of the invention to refer to relatively short fragments of single-stranded DNA used in the PCR amplification of specific regions of DNA.

"Phenotype" is understood within the scope of the invention to refer to a distinguishable characteristic(s) of a genetically controlled trait.

As used herein, the phrase "phenotypic trait" refers to the appearance or other detectable characteristic of an individual, resulting from the interaction of its genome, proteome and/or metabolome with the environment.

"Polymorphism" is understood within the scope of the invention to refer to the presence in a population of two or more different forms of a gene, genetic marker, or inherited trait or a gene product obtainable, for example, through alternative splicing, DNA methylation, etc.

"Selective breeding" is understood within the scope of the invention to refer to a program of breeding that uses plants that possess or display desirable traits as parents.

"Tester" plant is understood within the scope of the invention to refer to a plant of the genus *Lactuca* used to characterize genetically a trait in a plant to be tested. Typically, the plant to be tested is crossed with a "tester" plant and the segregation ratio of the trait in the progeny of the cross is scored.

"Probe" as used herein refers to a group of atoms or molecules which is capable of recognizing and binding to a specific target molecule or cellular structure and thus allowing detection of the target molecule or structure. Particularly, "probe" refers to a labeled DNA or RNA sequence which can be used to detect the presence of and to quantitate a complementary sequence by molecular hybridization.

"Sequence Homology or Sequence Identity" is used herein interchangeably. The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. If two sequences which are to be compared with each other differ in length, sequence identity preferably relates to the percentage of the nucleotide residues of the shorter sequence which are identical with the nucleotide residues of the longer sequence. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison may for instance be carried out by a Smith-Waterman BLAST alignment.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant materials" or "plant materials obtainable from a plant" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant or plant parts in culture is included. This term include, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

The terms "race" or "races" refer to any inbreeding group, including taxonomic subgroups such as subspecies, taxonomically subordinate to a species and superordinate to a subrace and marked by a pre-determined profile of latent factors of hereditary traits.

Downy mildew is a fungal disease caused by the fungus *Bremia lactucae*. It occurs worldwide and represents a huge problem for both the yield and quality of cultivated lettuce (*Lactuca sativa*). The fungus can infect the lettuce plant at any stage of growth, after which the first symptoms of downy mildew become visible as chlorotic yellow spots on the leaf surface. Within 24-48 hours a white fluffy fungus growth becomes visible on the lower leaf surface as an indication of spore formation. During the infection the spots of lesions become increasingly larger and more chlorotic until the leaves become completely brown. Typical sporulation occurs, when lettuce seedlings are susceptible to *Bremia lactucae*. In case plants are homozygous for the resistance trait, no sporulation is observed. When a semi-dominant resistance gene is heterozygous, also no sporulation is observed, but often yellowing or browning of cotyledons can be scored under ideal downy mildew *Bremia* incubation conditions.

*Bremia lactucae* belongs to the group Oomycetes, a class of relatively primitive fungi. Other members of this group are for instance *Pythium* and *Phytophthora*. B. laptucae contains different physiological species ("physio's"), is known as a very variable pathogen and is host-specific. New physio's occur relatively frequently through mutation of the virulence genes during spore formation preceding the propagation of *B. lactucae*. Currently there are 28 physio's known for *Bremia lactucae* (Bl:01 to Bl:28).

Within the genus *Lactucae*, to which the cultivated lettuce belongs, there are different species which are resistant to *Bremia lactucae*. The resistance is generally based on genes, known as Dm-resistance genes (Dm stands for Downy mildew). The resistance mechanism is known as gene-for-gene mechanism based on the specific interaction between products of the plant specific virulencegene and the pathogen-specific avirulence gene which results in resistance of the lettuce plant. The R-genes encode proteins with an extracellular nucleotide binding site (NBS), fused to a leucine-rich repeat (LRR) with different N-terminal domains (Toll-like TIR, X, Coiled CC). To date, the R-genes are grouped in 4/5 classes based on the conserved domain organization. If a Dm locus is dominant, no *Bremia* sporulation is observed.

Due to the high variablility of the pathogen, which is to be attributed to the occurrence of frequent mutations in the avirulence genes, the race-specific resistance mediated by the various Dm resistance genes is usually rapidly broken by newly emerging races or physios of the *Bremia lactucae* pathogen.

Because of reduced yield and quality of cultivated lettuce (*L. sativa*) caused by infestation of the lettuce plant with the fungus *Bremia lactucae*, there is an unmet need for convenient and economically sustainable strategies to protect plants, e.g. lettuce plants like *Lactuca*, against *Bremia lactucae* infestation.

The present invention addresses this need by providing a *L. sativa* plant, which is resistant to *Bremia lactucae* infestation and thus protected from damage caused by this pathogen. The provision of *Bremia lactucae* resistant lettuce is an environmentally friendly alternative for the use of pesticides and will contribute to successful integrated pest management programs. More preferably, said present invention relates to a plant and a method for providing resistance against *Bremia lactucae* races Bl:1 to Bl:28 in lettuce.

The technical problem underlying the present invention is, therefore, the provision of a *Bremia lactucae* resistant *L. sativa* plant, which shows an improved resistance, particularly a general, race non-specific resistance to this pathogen in terms of races known as of the filing date of the present application, particularly to (at least) *Bremia* races or isolates Bl:01 to Bl:28 characterized and classified according to the SEXTET code by IBEB (International *Bremia* Evaluation Board).

The technical problem is solved by the provision of the embodiments characterized in the claims. Moreover, it was now surprisingly found within the scope of the present invention that the linkage between genes responsible for undesired, morphological changes at the plant and the gene responsible for the resistance to *Bremia lactucae* as present in the wild-type source material, is broken and thus no longer present in the *Lactuca sativa* plant according to the invention.

In a first embodiment, the present invention relates to a *Lactuca sativa* plant resistant to *Bremia lactucae*. The *Lactuca sativa* plant according to the current invention will preferably comprise a *Bremia lactucae* resistance locus, particularly a *Bremia* resistance locus, particularly a broad-spectrum *Bremia lactucae* resistance locus, linked to a genetic determinant and obtainable from the genome of a wild *Lactuca* plant, particularly from the genome of *Lactuca serriola*. In a specific embodiment of the invention, the resistance to *Bremia lactucae* is a general, race non-specific resistance. In a further specific embodiment of the invention, it is aimed to reduce linkage drag or co-expression of agronomical undesirable traits such as, for example dwarfism, to a minimum. The latter is by preference obtained by back crossing with the recurrent Parent, e.g. L. *Sativa* ssp. In one embodiment, the present invention contemplates a plant wherein the *Bremia lactucae* resistance locus is present in a homozygous state.

In an embodiment of the present invention, said *Bremia lactucae* resistance locus is located on a specific linkage group. By preference, said resistance locus is located on linkage group 2.

More preferably, said resistance locus co-segregates with a sequence which has at least 90% homology, more preferably at least 95%, even more preferably at least 98%, more preferably at least 99%, most preferably 100% with a sequence chosen from SEQ ID No. 1 or SEQ ID No. 2.

In a further embodiment, the present invention also contemplates a plant according to any of the preceding embodiments wherein the presence of the *Bremia lactucae* resistance locus is characterized by at least one DNA or determinant marker on the chromosome that is statistically correlated and thus genetically linked to the *Bremia lactucae* resistance trait.

Preferably, said DNA or determinant marker has at least 90% homology, more preferably at least 95%, more preferably at least 98%, more preferably at least 99%, most preferably 100% homology with a sequence chosen from SEQ ID No. 1 or SEQ ID No. 2.

In another embodiment, the present invention also relates to a *L. sativa* plant according to any of the preceding embodiments, wherein the *Bremia lactucae* resistance locus in *L. serriola* is genetically linked to at least one marker locus, which co-segregates with the *Bremia lactucae* resistance trait. By preference, such marker locicomprises DNA base variations such as single-nucleotide polymorphisms (SNPs), microsatellite or simple sequence repeats (SSRs). Said marker loci has at least 90% homology, more preferably at least 95%, more preferably at least 98%, more preferably at least 99%, most preferably 100% homology with a sequence chosen from SEQ ID No. 1 or SEQ ID No. 2.

In a further embodiment, a *L. sativa* plant is provided comprising at least one allele at a R-gene locus in the *L. sativa* genome contributing to resistance to *Bremia lactucae*, which is genetically linked to at least one marker locus, which co-segregates with the *Bremia lactucae* resistance trait and that can be identified by at least one PCR oligonucleotide primer or by any other marker on the chromosome that is statistically correlated and thus genetically linked to the *Bremia lactucae* resistance trait. By preference, such locus is located on linkage group 2.

The nucleic acid sequence of markers, linked markers or the *Bremia lactucae* resistance locus may be determined by methods known to the skilled person. For example, a nucleic acid sequence comprising said *Bremia lactucae* resistance locus or a resistance-conferring part thereof may be isolated from a *Bremia lactucae* resistant donor plant by fragmenting the genome of said plant and selecting those fragments harbouring one or more markers indicative of said *Bremia lactucae* resistance locus. Subsequently, or alternatively, the marker sequences (or parts thereof) indicative of said resistance locus may be used as (PCR) amplification primers, in order to amplify (a) nucleic acid sequence(s) comprising said resistance locus from a genomic nucleic acid sample or a genome fragment obtained from said plant. The nucleotide sequence of the *Bremia lactucae* resistance locus, and/or of any additional marker comprised therein, may be obtained by standard sequencing methods. For further details, see example 3.

In one embodiment, said allele at the resistance (R)-gene locus in the *L. sativa* genome contributing to resistance to *Bremia lactucae*, is obtainable from a plant which has the genetic background of *Lactuca sativa* line AS-002, particularly from a plant which has the genetic background or architecture at the R-gene locus of *L. sativa* line AS-002, but especially from a *Lactuca sativa* line AS-002, representative seed of which is deposited at NCIMB under Accession No. NCIMB 42082, or from a progeny or an ancestor thereof comprising said R-gene locus.

In another embodiment as described herein, a *Lactuca sativa* plant is provided comprising at least one allele or part thereof at a R-gene locus in the *L. sativa* genome contributing to resistance to *Bremia lactucae*, which is complementary to the corresponding allele present in a *Lactuca sativa* line AS-002, deposited under Accession No. NCIMB 42082, and genetically linked to at least one marker locus within the *Lactuca serriola* genome, which co-segregates with the *Bremia* resistance trait and can be identified by at one marker determinant on the chromosome that is statistically correlated and thus genetically linked to the *Bremia lactucae* resistance trait as described. Said marker determinant is homologous or identical to SEQ ID No. 1 or SEQ ID No. 2.

In a further embodiment, the present invention also relates to a plant according to any of the preceding embodiments, wherein said plant is a dihaploid or a hybrid.

In another embodiment, a plant according to any of the preceding embodiments is also contemplated, wherein said plant is male sterile.

In one aspect of the invention, the *L. sativa* plant according to the invention and as described herein before is heterozygous for the *Bremia lactucae* resistance trait.

In one aspect of the invention, the *L. sativa* plant according to the invention and as described herein before is homozygous for the *Bremia lactucae* resistance trait.

A specific embodiment of the invention relates to a *L. sativa* plant according to the invention and as described herein before capable of resisting infestations with *Bremia lactucae*, which plant is a plant of a cultivar group selected from butterhead, Chinese lettuce, crisphead (Iceberg forms), looseleaf, Romaine, and summer crisp.

In a further embodiment, the present invention relates to plant material obtainable from a plant according to any of the preceding embodiments including, but without being limited thereto, leaves, stems, roots, flowers or flower parts, fruits, pollen, egg cells, zygotes, seeds, cuttings, cell or tissue cultures, or any other part or product of the plant which still exhibits the resistant phenotype according to the invention, particularly when grown into a plant.

In another embodiment as described herein, plant parts of a plant according to any of the preceding embodiments are provided including, but without being limited thereto, plant seed, plant organs such as, for example, a root, stem, leaf, flower bud, or embryo, etc, ovules, pollen microspores, plant cells, plant tissue, plant cells cultures such as, for example, protoplasts, cell culture cells, cells in plant tissues, pollen, pollen tubes, ovules, embryo sacs, zygotes and embryos at various stages of development, etc; which still exhibits the resistant phenotype according to the invention, particularly when grown into a plant.

In a further embodiment of the present invention, a seed of a homozygous plant according to any of the preceding embodiments is also provided.

In another embodiment, the present invention further contemplates seeds of a *L. sativa* plant as claimed in any of the preceding embodiments, particularly hybrid seed, comprising the genetic determinant contributing to resistance to *Bremia lactucae*.

In another embodiment, the present invention relates to seeds according to any of the preceding embodiments, deposited at the NCIMB Ltd. under Accession No. NCIMB 42082.

In a further embodiment, seeds according to any of the preceding embodiments are provided by the present invention, wherein said genetic determinant contributes to *Bremia lactucae* resistance provides resistance to at least *Bremia lactucae* races Bl:1 to Bl:28. Preferably, said genetic determinant is located on linkage group 2.

The present invention also contemplates the use of *L. sativa* to produce seed comprising the genetic determinant contributing to resistance to *Bremia lactucae*, particularly to at least *Bremia lactucae* races Bl:1 to Bl:28.

In still another embodiment of the present invention, a DNA marker is provided that is linked to the *Bremia lactucae* resistance locus and can be amplified by at least one oligonucleotide primer or by any other marker determinant on the chromosome that is statistically correlated and thus genetically linked to the *Bremia lactucae* resistance trait and which is able to amplify a DNA marker linked to the *Bremia lactucae* resistance locus. In another embodiment, the present invention relates to the haploid type of which can be detected by the use of aforementioned marker. Said marker has at least 90% homology, more preferably at least 95%, more preferably at least 98%, more preferably at least 99%, most preferably 100% homology with a sequence chosen from SEQ ID No. 1 or SEQ ID No. 2.

In a further embodiment, the present invention relates also to the use of some or all of these DNA markers for diagnostic selection of a lettuce *Bremia* resistance locus, particularly the as002 *Bremia* resistance locus, in *L. sativa*.

In another embodiment, the present invention further contemplates the use of some or all of these DNA markers for identifying in a plant the presence of the *Bremia lactucae* resistance locus and/or for monitoring the introgression of the lettuce *Bremia lactucae* resistance locus in *Lactuca sativa*.

The present invention therefore further relates in one embodiment to derived markers, developed from an amplification product according to the invention and as described herein above by methods known in the art, which derived markers are genetically linked to the *Bremia lactucae* resistance locus, particularly the as002 *Bremia lactucae* resistance locus, in *L. sativa*.

These derived markers can then be used to identify *Bremia lactucae* resistant plants, wherein the markers specifically referred to herein are recombined relative to the resistance and thus no longer present in the resistant plant genome which was used for introgression.

In a further embodiment, a method is provided within the present invention for introducing at least one allele associated with resistance to *Bremia lactucae* at a R-gene locus contributing to resistance to *Bremia* into a *L. sativa* plant lacking said allele comprising: a) obtaining a first *L. sativa* plant according to any one of the preceding claims; b) crossing said first *L. sativa* plant with a second *L. sativa* plant, wherein said second *L. sativa* plant lacks said allele; and c) identifying a plant resulting from the cross exhibiting increased resistance to *Bremia lactucae* and comprising at least one marker determinant co-segregating with said *Bremia* resistance; and d) optionally, isolating said plant and e) optionally, back-crossing said plant with the first or second *L. sativa* plant. Said marker determinant has at least 90% homology, more preferably at least 95%, more preferably at least 98%, more preferably at least 99%, most preferably 100% homology with a sequence chosen from SEQ ID No. 1 or SEQ ID No. 2.

In a further embodiment, the present invention relates also to a method of obtaining a *Lactuca sativa* plant resistant against *Bremia lactucae*, comprising: a) obtaining a F1-hybrid by crossing a *Lactuca serriola* plant with a *Lactuca sativa* plant, which is sensitive to infestation with *Bremia lactucae*; b) backcrossing the F1-hybrid with said *Lactuca sativa* plant; and c) identifying a plant resulting from the cross exhibiting resistance to *Bremia lactucae* and comprising at least one marker determinant co-segregating with said *Bremia* resistance, and d) optionally, growing said plant. Said marker determinant has at least 90% homology, more preferably at least 95%, more preferably at least 98%, more preferably at least 99%, most preferably 100% homology with a sequence chosen from SEQ ID No. 1 or SEQ ID No. 2.

In another embodiment, a method is contemplated herein for obtaining seed according to any of the preceding embodiments comprising the steps of: a) obtaining a first *L. sativa* plant according to any one of the preceding claims; b) crossing said first *L. sativa* plant with a second *L. sativa* plant, wherein said second *L. sativa* plant lacks said allele; and c) identifying a plant resulting from the cross exhibiting resistance to *Bremia lactucae* and comprising at least one marker determinant co-segregating with said *Bremia lactucae* resistance; and d) harvesting progeny seed from said cross comprising at least one marker determinant co-segregating with said *Bremia lactucae* resistance.

In a further embodiment, the present invention also relates to a method according to any of the preceding embodiments, wherein in step c) the plant resulting from any of the above crosses is identified by applying phenotypic selection based on the plants exhibiting an increased resistance to *Bremia lactucae* or by a combination of a PCR-based and a phenotypic selection.

In a further embodiment, a method of protecting a *Lactuca sativa* plant against infestation with *Bremia lactucae* is provided herein, comprising a) obtaining a *Lactuca sativa* plant resistant to *Bremia lactucae* according to any one of the preceding embodiments; and b) growing said plant in an area with high disease (*Bremia lactucae*) pressure.

In another embodiment of the present invention, the use of a seed according to any one of the preceding embodiments is contemplated for growing a *Lactuca sativa* plant resistant to *Bremia lactucae*.

Plants Derived from *Lactuca sativa* Line AS-002 by Genetic Engineering

Many useful traits that can be introduced by backcrossing, as well as directly into a plant, are those which are introduced by genetic transformation techniques. Genetic transformation may therefore be used to insert a selected transgene into the *L. sativa* line of the invention or may, alternatively, be used for the preparation of transgenes which can be introduced by backcrossing. Methods for the transformation of plants, including *L. sativa*, are well known to those of skill in the art. Techniques which may be employed for the genetic transformation of *L. sativa* include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

Production of transgenic lettuce plants, including at least *Lactuca sativa*, have been established. An exemplary protocol for transforming transgenic *L. sativa* with *Agrobacterium tumefaciens* is described by Ian S. Curtis (Methods in Molecular Biology, volume 343, p. 449-458, Jun. 1, 2006).

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target *L. sativa* cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the *facile* and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for *L. sativa* plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the *L. sativa* lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

In an embodiment of the current invention, the resistance locus identified in *Lactuca serriola* can be isolated from a *Lactuca serriola* plant and stably inserted through suitable transgenic techniques as described above in to the genome of a *Lactuca sativa* plant. Preferably, the transferred transgene comprises both the resistance locus bearing the as-002 locus as well as the genetically linked marker locus as defined above As mentioned, the present invention relates to novel *Lactuca sativa* plants, which are resistant to *Bremia lactucae* infestation and thus protected from damage caused by this pathogen. The present invention also relates to methods of making and using such plants.

Plants according to the invention may be obtained by crossing two or more parental genotypes, at least one of which may have one or more alleles, particularly one or more alleles at corresponding R-gene loci contributing to *Bremia lactucae* resistance, which allele(s) is/are lacking in the other parental genotype or which complements the other genotype to obtain a plant according to the invention and as described herein before. If more than one R-gene loci contribute to the expression of the resistance trait and the two original parental genotypes do not provide the entire set of alleles, other sources can be included in the breeding population. The other parental genotype may contribute a desirable trait including, crop quality demanded by the market such as, for example, increased head size and weight, higher seed yield, improved or deep green exterior color, tolerance to drought and heat and as well as improved agronomical qualities.

In iceberg lettuce, for example, desired traits comprise tight and dense head that resembles a cabbage. Iceberg lettuces are generally mild in flavour, provide a crunchy texture and exhibit a white or creamy yellow interior. Battavian lettuces are close to iceberg while being characterized by a smaller and less firm head. Regarding butterhead lettuce, these are characterized by a smaller head much more soft and oily and buttery texture. Eventually romaine lettuce has elongated upright crunchy leaves forming a loaf-shaped head with dark green outer leaves.

Beside crop quality, agronomically important characteristics such as, for example, a good plant architecture, high productivity and basic resistances to disease such as, but not limited to, Lettuce Mosaic Virus (LMV), *Nasonovia*, root aphids, Beet Western Yellow Virus (BMYV), Turnip Mosaic Virus (TMV) are further desired traits.

In a particular embodiment of the invention, a downy mildew resistance gene has been identified in a wild lettuce *Lactuca serriola*, which confers full resistance to all known *Bremia* races to date (28). It was introgressed by backcrossing in cultivated *L. sativa*. Extensive F2 and F3 population *Bremia* seedling disease tests indicated that resistance is caused by a major (semi-)dominant gene. This *L. serriola*-derived resistance ("as002") may be combined with other known in the art *Bremia* resistances like R17, R18, R36, R38 or Dm3. Said as002 was found to be located on linkage group 2.

The parental genotypes may be crossed with one another to produce progeny seed. The parental genotypes may be inbred lines developed by selfing selected heterozygous plants from fields with uncontrolled or open pollination and employing recurrent selection procedures. Superior plants are selfed and selected in successive generations. In the succeeding generations the heterozygous condition gives way to homogeneous lines as a result of self-pollination and selection. With successive generations of inbreeding, the plant becomes more and more homozygous and uniform within the progeny plants. Typically, five to seven or more generations (F1 to F2; F3 to F4; F4 to F5) of selfing and pedigree selection may be practiced to obtain inbred lines that are uniform in plant and seed characteristics and that will remain uniform under continued self-fertilization.

During inbreeding, many undesirable alleles at heterozygous loci will be replaced by more favourable alleles and the unfavourable or undesired alleles eliminated from the progeny Moreover, through marker-assisted selection the number of favorable alleles can be maximized in that the more unfavourable alleles are identified and successively replaced by the more favorable alleles.

In one aspect, the plant according to the invention may be obtained by introgressing the *Bremia* resistance trait from an ancestor plant, particularly a wild ancestor plant into a cultivated lettuce plant, particularly a *Lactuca sativa* plant, more particularly a cultivated *Lactuca sativa* plant.

In one specific embodiment of the invention, the wild ancestor, from which the *Bremia lactucae* resistance trait may be obtained, is wild *Lactuca*, particularly wild *Lactuca serriola* or from a progeny or an ancestor thereof comprising said R-gene locus. The resistance trait according to the present invention, which confers to a plant expressing this trait, resistance to infestations with the fungus *Bremia lactucae*, may, in the alternative, be obtained from *Lactuca sativa* line AS-002, representative seed of which is deposited at NCIMB under Accession No. NCIMB 42082, or from a progeny or ancestor of line AS-002 comprising the *Bremia lactucae* resistance trait.

Accordingly, in a specific embodiment of the invention, the parental genotype contributing the resistance trait(s) is an inbred line having the invention relevant properties of deposited *Lactuca sativa* line AS-002, i. e. substantially the same genome architecture at the R-gene locus associated with *Bremia* resistance, seed samples of which have been deposited on Nov. 13, 2012 with NCIMB under accession number NCIMB 42082.

To determine the utility of the inbred line and its potential to genetically contribute to the hybrid progeny a test-cross is made with another inbred line, and the resulting progeny phenotypically devaluated.

In another specific embodiment of the invention, the parental genotype contributing to the resistance trait(s) is a hybrid having the invention relevant properties of deposited *Lactuca sativa* line AS-002, i. e. substantially the same genome architecture at the R-gene locus associated with *Bremia* resistance, seed samples of which have been deposited on Nov. 13, 2012 with NCIMB under accession number NCIMB 42082.

*Lactuca sativa* line AS-002 resulted from a cross of a wild *Lactuca serriola*, as the donor of the resistance trait with a *Lactuca sativa* inbred line. *Bremia* resistant progeny of this cross was crossed with further inbred lines of different genetic backgrounds to finally obtain *Lactuca sativa* line AS-002.

Accordingly, *Lactuca sativa* line AS-002 or any other plant line containing the *Bremia* resistance trait may be used as a source material for introgressing said resistance trait into any desired genetic background to obtain a lettuce plant being highly resistant to infestations with the a fungus of the genus *Bremia*, more particularly to infestations with *Bremia lactucae*, may further contain one or more desirable traits such as crop quality traits demanded by the market. Beside crop quality, agronomically important characteristics such as, for example, a good plant architecture, high productivity and basic resistances to relevant pathogens such as Lettuce Mosaic Virus (LMV), *Nasonovia*, root aphids, Beet Western Yellow Virus (BMYV), Turnip Mosaic Virus (TMV) are further desired traits.

Based on the description of the present invention, the skilled person who is in possession of *Lactuca sativa* line AS-002, a sample of which has been deposited with NCIMB Ltd under accession number NCIMB 42082 or of a progeny or ancestor thereof containing a R-gene locus on the linkage group associated with resistance to *Bremia*, as described herein, has no difficulty to transfer the *Bremia* resistance trait of the present invention to other lettuce plants of various types using breeding techniques well-known in the art. The trait of the present invention may for example be transferred to lettuce plants of the following cultivar groups: butterhead, Chinese lettuce, crisphead (Iceberg forms), losseleaf, Romaine, summer crisp. Accordingly, in one embodiment, a plant of the present invention is a *L. sativa* plant capable of resisting infestations with *Bremia*, which plant is a plant of the cultivar group selected from the group consisting of butterhead, Chinese lettuce, crisphead (Iceberg forms), looseleaf, Romaine, and summer crisp. In one embodiment of the invention, the aforementioned lettuce plants are grown for (hybrid) seed or commercial lettuce production.

Accordingly, in another embodiment, the present invention discloses a method of transferring the *Bremia lactucae* resistance trait according to the present invention to a lettuce plant lacking said trait comprising a) obtaining a plant comprising said trait; b) crossing it to a plant lacking said trait; c) obtaining plants of the cross of step b); d) selecting a plant of step c) which is capable of resisting infestations with *Bremia lactucae* according to the present invention. In one embodiment, the method further comprises e) back-crossing a plant resulting from step d) with a lettuce plant, and f) selecting for a lettuce plant, which is capable of resisting infestations with *Bremia lactucae* according to the present invention. In one embodiment, the method further comprises obtaining an inbred lettuce plant, which is capable of resisting infestations with *Bremia* according to the present invention, and, in one embodiment, the method further comprises crossing said inbred lettuce plant to another lettuce plant to produce a hybrid lettuce plant, which is capable of resisting infestations with *Bremia lactucae* according to the present invention. In one embodiment, a lettuce plant is selected by determining presence or absence of the fungus, as described herein. In a preferred embodiment, the plant of step a) comprising said trait is *Lactuca sativa* line AS-002, representative seed of which is deposited at NCIMB under Accession No. NCIMB 42082, or a progeny or ancestor of said plant.

In certain embodiments of the invention, a standardized Resistance Assay is used, such as that described in Example 1 herein below, to determine presence of absence of a resistance against *Bremia lactucae* in the progeny plants resulting from one of the above crosses and to select those progeny plants for further breeding which are resistant, to *Bremia lactucae*.

In the alternative, marker-assisted breeding may be employed to identify those individuals which contain the *Bremia lactucae* resistance locus, and/or flanking marker loci or marker loci genetically linked thereto, as described herein.

Marker-assisted selection may already be used in the early phases of inbred development, often in combination with screening methods which are based largely on phenotypic characteristics that can be determined visually and are related to key performance indices such as, for example, plant vigor, length of internodes, ramifications, resistance to insects or fungi, such as resistance to *Bremia* infestations, virus resistances, etc., which are relevant for the suitability of the plant to be utilized in commercial hybrid production. Selection may also be based on molecular markers, which may or may not be linked to traits of interest.

In particular, marker-assisted selection may be applied in combination with or followed by a phenotypic selection to identify those individuals where all of the invention relevant loci described herein before have homozygous favorable genotypes.

There are several types of molecular markers that may be used in marker-assisted selection including, but not limited to, restriction fragment length polymorphism (RFLP), random amplification of polymorphic DNA (RAPD), amplified restriction fragment length polymorphism (AFLP), single sequence repeats (SSR) and single nucleotide polymorphism SNPs.

RFLP involves the use of restriction enzymes to cut chromosomal DNA at specific short restriction sites, polymorphisms result from duplications or deletions between the sites or mutations at the restriction sites.

RAPD utilizes low stringency polymerase chain reaction (PCR) amplification with single primers of arbitrary sequence to generate strain-specific arrays of anonymous DNA fragments. The method requires only tiny DNA samples and analyses a large number of polymorphic loci.

AFLP requires digestion of cellular DNA with a restriction enzyme(s) before using PCR and selective nucleotide in the primers to amplify specific fragments. With this method, using electrophoresis techniques to visualize the obtained fragments, up to 100 polymorphic loci can be measured per primer combination and only small DNA sample are required for each test.

SSR analysis is based on DNA micro-satellites (short-repeat) sequences that are widely dispersed throughout the genome of eukaryotes, which are selectively amplified to detect variations in simple sequence repeats. Only tiny DNA samples are required for an SSR analysis. SNPs use PCR extension assays that efficiently pick up point mutations. The procedure requires little DNA per sample. One or two of the above methods may be used in a typical marker-assisted selection breeding program.

The most preferred method of achieving amplification of nucleotide fragments that span a polymorphic region of the plant genome employs the polymerase chain reaction ("PCR") (Mullis et al., Cold Spring Harbor Symp. Quaint. Biol. 51:263 273 (1986)), using primer pairs involving a forward primer and a backward primer that are capable of hybridizing to the proximal sequences that define a polymorphism in its doubles-stranded form.

Alternative methods may be employed to amplify fragments, such as the "Ligase Chain Reaction" ("PCR") (Barany, Proc. Natl. Acad. Sci. (U.S.A.) 88:189 193 (1991)), which uses two pairs of oligonucleotide probes to exponentially amplify a specific target. The sequences of each pair of oligonucleotides are selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

LCR can be performed with oligonucleotides having the proximal and distal sequences of the same strand of a polymorphic site. In one embodiment, either oligonucleotide will be designed to include the actual polymorphic site of the polymorphism. In such an embodiment, the reaction conditions are selected such that the oligonucleotides can be ligated together only if the target molecule either contains or lacks the specific nucleotide that is complementary to the polymorphic site present on the oligonucleotide. Alternatively, the oligonucleotides may be selected such that they do not include the polymorphic site (see, Segev, PCT Application WO 90/01069).

A further method that may alternatively be employed is the "Oligonucleotide Ligation Assay" ("OLA") (Landegren et al., Science 241:1077 1080 (1988)). The OLA protocol uses two oligonucleotides that are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Still another method that may alternatively be employed is the "Invader Assay" that uses a structure-specific flap endonuclease (FEN) to cleave a three-dimensional complex formed by hybridization of allele-specific overlapping oligonucleotides to target DNA containing a single nucleotide polymorphism (SNP) site. Annealing of the oligonucleotide complementary to the SNP allele in the target molecule triggers the cleavage of the oligonucleotide by cleavase, a thermostable FEN. Cleavage can be detected by several different approaches. Most commonly, the cleavage product triggers a secondary cleavage reaction on a fluorescence resonance energy transfer (FRET) cassette to release a fluorescent signal. Alternatively, the cleavage can be detected directly by use of fluorescence polarization (FP) probes, or by mass spectrometry. The invasive cleavage reaction is highly specific, has a low failure rate, and can detect zeptomol quantities of target DNA. While the assay traditionally has been used to interrogate one SNP in one sample per reaction, novel chip- or bead-based approaches have been tested to make this efficient and accurate assay adaptable to multiplexing and high-throughput SNP genotyping.

Nickerson et al. have described a nucleic acid detection assay that combines attributes of PCR and OLA (Nickerson et al., Proc. Natl. Acad. Sci. (U.S.A.) 87:8923 8927 (1990)). In this method, PCR is used to achieve the exponential amplification of target DNA, which is then detected using OLA.

Schemes based on ligation of two (or more) oligonucleotides in the presence of a nucleic acid having the sequence of the resulting "di-oligonucleotide", thereby amplifying the di-oligonucleotide, are also known (Wu et al., Genomics 4:560 569 (1989)), and may be readily adapted to the purposes of the present invention.

In one embodiment, a molecular marker is a DNA fragment amplified by PCR, e.g. a SSR marker or a RAPD marker. In one embodiment, the presence or absence of an amplified DNA fragment is indicative of the presence or absence of the trait itself or of a particular allele of the trait. In one embodiment, a difference in the length of an amplified DNA fragment is indicative of the presence of a particular allele of a trait, and thus enables to distinguish between different alleles of a trait.

In a specific embodiment of the invention simple sequence repeat (SSR) markers are used to identify invention-relevant alleles in the parent plants and/or the ancestors thereof, as well as in the progeny plants resulting from a cross of said parent plants. Simple sequence repeats are short, repeated DNA sequences and present in the genomes of all eukaryotes and consists of several to over a hundred repeats of a given nucleotide motif. Since the number of repeats present at a particular location in the genome often differs among plants, SSRs can be analyzed to determine the absence or presence of specific alleles.

In another embodiment of the invention SNP markers are used to identify invention-relevant alleles in the parent plants and/or the ancestors thereof, as well as in the progeny plants resulting from a cross of said parent plants.

In the present invention a marker or a set of two or more markers may be used comprising a pair of PCR oligonucleotides primers consisting of a forward primer and a reverse primer which primers lead to an amplification product in a PCR reaction exhibiting a molecular weight or a nucleotide sequence, which is essentially identical or can be considered as an allele to that of a corresponding PCR amplification product obtainable from *Lactuca sativa* line AS-002 in a PCR reaction with the identical primer pair(s).

Preferably, said marker has at least 90% homology, more preferably at least 95%, more preferably at least 98%, more preferably at least 99%, most preferably 100% homology with a sequence chosen from SEQ ID No. 1 or SEQ ID No. 2. More preferably, said marker is a SNP marker In a first step, DNA or cDNA samples are obtained from suitable plant material such as leaf tissue by extracting DNA or RNA using known techniques. Primers that flank a region containing SSRs within the invention-relevant R-gene locus before or within a region linked thereto are then used to amplify the DNA sample using the polymerase chain reaction (PCR) method well-known to those skilled in the art.

Basically, the method of PCR amplification involves use of a primer or a pair of primers comprising two short oligonucleotide primer sequences flanking the DNA segment to be amplified or adapter sequences ligated to said DNA segment. Repeated cycles of heating and denaturation of the DNA are followed by annealing of the primers to their complementary sequences at low temperatures, and extension of the annealed primers with DNA polymerize. The primers hybridize to opposite strands of the DNA target sequences. Hybridization refers to annealing of complementary DNA strands, where complementary refers to the sequence of the nucleotides such that the nucleotide of one strand can bond with the nucleotide on the opposite strand to form double stranded structures. The primers are oriented so that DNA synthesis by the polymerase proceeds bidirectionally across the nucleotide sequence between the primers. This procedure effectively doubles the amount of that DNA segment in one cycle. Because the PCR products are complementary to, and capable of binding to, the primers, each successive cycle doubles the amount of DNA synthesized in the previous cycles. The result of this procedure is exponential accumulation of a specific target fragment, that is approximately 2<n>, where n is the number of cycle.

Through PCR amplification millions of copies of the DNA segment flanked by the primers are made. Differences in the number of repeated sequences or insertions or deletions in the region franking said repeats, which are located between the flanking primers in different alleles are reflected in length variations of the amplified DNA fragments. These variations can be detected, for example, by electrophoretically separating the amplified DNA fragments on gels or by using capillary sequencer. By analyzing the gel or profile, it can be determined whether the plant contains the desired allele in a homozygous or heterozygous state or whether the desired or undesired allele is absent from the plant genome.

In the alternative, the presence or absence of the desired allele may be determined by real-time PCR using double-stranded DNA dyes or the fluorescent reporter probe method. It should be stressed that the aforementioned are merely given as an example and should in no way be construed as limiting to the current invention.

Marker analysis can be done early in plant development using DNA samples extracted from leaf tissue of very young plants or from seed. This allows to identify plants with a desirable genetic make-up early in the breeding cycle and to discard plants that do not contain the desired, invention-relevant alleles prior to pollination thus reducing the size of the breeding population and reducing the requirements of phenotyping.

Further, by using molecular markers, it might be possible to distinguish between homozygous plants that carry two copies of the desired, invention-relevant allele ('as-002 allele') at the *Bremia* resistance qualitative locus and heterozygous plant that carry only one copy and plants that do not contain any copy of the favourable allele(s).

Thus, alternative markers can therefore be developed by methods known to the skilled person and used to identify and select plants with an allele or a set of alleles of a R-gene locus or loci according to the present invention and as disclosed herein before.

For example, the nucleotide sequence of the amplification product obtained in PCR amplification using a pair of PCR oligonucleotide primers consisting of a forward primer and a reverse primer can be obtained by those skilled in the art and new primers or primer pairs designed based on the newly determined nucleotide sequence of the PCR amplification product. Accordingly, markers usable in the present invention may also be used in the identification and/or development of new or additional markers associated with the *Bremia* resistance locus, which in turn can then be used in marker assisted breeding and/or the search of recombinants flanking the *Bremia lactucae* resistance locus, and/or fine-mapping, and/or cloning of the *Bremia lactucae* resistance locus.

There are several methods or approaches available, known to those skilled in the art, which can be used to identify and/or develop markers in linkage disequilibrium and/or linked to and/or located in the region of interest, as well as markers that represent the actual causal mutations underlying the R-gene. As used herein, 'linkage disequilibrium' is the non-random association of alleles at two or more loci, that may or may not be on the same chromosome. Without being fully exhaustive some approaches, known by those skilled in the art, include:

- use of disclosed sequences/markers in PCR approaches to identify other sequence in the region of interest: primer sequences as disclosed herein and/or marker/-(candidate)gene sequences (or part thereof) that can be determined using the primer sequences as disclosed may be used as (PCR) amplification primers to amplify a nucleic acid sequence/gene flanking and/or linked to and/or associated with and/or specific for the region of the *Bremia* resistance locus from a genomic nucleic acid sample and/or RNA or cDNA sample or pool of samples either or not isolated from a specific plant tissue and/or after specific treatment of the plant and from *capsicum* or in principal any other organism with sufficient homology.
- use of disclosed sequences/markers in PCR approaches to identify other sequence in the region of interest: the nucleotide sequences/genes of one or more markers can be determined after internal primers for said marker sequences may be designed and used to further determine additional flanking sequence/genes within the region of the *Bremia* resistance locus and/or genetically linked and/or associated with the trait.
- use of disclosed sequences/markers in mapping and/or comparative mapping approaches to identify markers in the same region(s) (positioning of the *Bremia* resistance locus on other maps): based on positional information and/or marker information as disclosed herein, markers, of any type, may be identified by genetic mapping approaches, eventually (if already needed) by positioning of the disclosed markers (by genetic mapping or extrapolation based on common markers across maps) on a (high density) genetic map(s), and/or integrated genetic or consensus map(s). Markers already known and/or new markers genetically linked and/or positioned in the vicinity of the disclosed markers and/or the region of the *Bremia* resistance locus may be identified and/or obtained and eventually used in (fine-) mapping and/or cloning of the *Bremia* resistance locus and/or MAS breeding applications.
- use of disclosed sequences/markers in 'in-silico' approaches to identify additional sequences/markers/(candidate)genes: Primer sequences as disclosed herein and/or marker/(candidate)gene sequences (or part thereof) that can be determined using the primer sequences as disclosed herein or based on linked markers may be used in 'in-silico' methods to search sequence or protein databases (e.g. BLAST) for (additional) flanking and/or homolog sequences/genes and/ or allelic diversity (both genomic and/or cDNA sequences or even proteins and both originating from *capsicum* and/or any other organism) genetically linked and/or associated with the traits as described herein and/or located in the region of the *Bremia* resistance locus.

use of disclosed sequences/markers in physical mapping approaches (positioning of the *Bremia* resistance locus on physical map or genome sequence): primer sequences as disclosed herein and/or marker/gene sequences (or part thereof) that can be determined using the primer sequences as disclosed herein or using other markers genetically linked to the markers disclosed herein and/or located in the region of the *Bremia* resistance locus may be positioned on a physical map and/or (whole) genome sequence in principal of any organism with sufficient homology to identify (candidate) sequences/markers/genes applicable in (fine-mapping) and/or cloning of the *Bremia* resistance locus and/or MAS breeding applications.

use of disclosed sequences/markers to position the *Bremia lactucae* resistance locus on other (physical) maps or genomes (across species for lettuce other Asteraceae species may be used as model species): primer sequences as disclosed herein and/or marker/gene sequences (or part thereof) that can be determined using the primer sequences as disclosed herein may be used in comparative genomics or syntheny mapping approaches to identify homolog region and homolog and/or orthologue sequences/(candidate)genes genetically linked and/or positioned in the region of the *Bremia lactucae* resistance locus and applicable in (fine-mapping) and/or cloning of the *Bremia lactucae* resistance locus and/or MAS breeding applications.

use of disclosed sequences/markers to select the appropriate individuals allowing the identification of markers in region of interest by genetic approaches: primer sequences and/or markers as disclosed herein may be used to select individuals with different/contrasting alleles which in for example in genetic association approaches and/or bulk segregant analysis (BSA, Michelmore et al., PNAS, 88, 9828-9832, 1991) can be used to identify markers/genes in the specific region of interest and/or associated or genetically linked to the described traits.

For genotyping, mapping or association mapping, DNA is extracted from suitable plant material such as, for example, leaf tissue. In particular, bulks of leaves of a plurality of plants are collected. DNA samples are genotyped using a plurality of polymorphic SSR's, SNPs or any other suitable marker-type covering the entire lettuce genome.

Joint-analysis of genotypic and phenotypic data can be performed using standard software known to those skilled in the art. Plant introductions and germplasm can be screened for the alleles at the corresponding *Bremia lactucae* resistance locus disclosed herein, based on the nucleotide sequence(s) of the marker(s) at the marker locus/loci linked to said *Bremia lactucae* resistance locus or any other marker known to be located on the chromosome responsible for the *Bremia lactucae* resistance, and the molecular weight of the allele(s) using one or more of the techniques disclosed herein or known to those skilled in the art.

The nucleic acid sequence of markers, linked markers or the *Bremia lactucae* resistance locus may be determined by methods known to the skilled person. For example, a nucleic acid sequence comprising said *Bremia lactucae* resistance locus or a resistance-conferring part thereof may be isolated from a *Bremia lactucae* resistant donor plant by fragmenting the genome of said plant and selecting those fragments harbouring one or more markers indicative of said *Bremia lactucae* resistance locus. Subsequently, or alternatively, the marker sequences (or parts thereof) indicative of said resistance locus may be used as (PCR) amplification primers, in order to amplify (a) nucleic acid sequence(s) comprising said resistance locus from a genomic nucleic acid sample or a genome fragment obtained from said plant. The nucleotide sequence of the *Bremia lactucae* resistance locus, and/or of any additional marker comprised therein, may be obtained by standard sequencing methods.

The present invention therefore also relates to an isolated nucleic acid (preferably DNA but not limited to DNA) sequence that comprises a *Bremia* resistance locus of the present invention, or a resistance-conferring part thereof. The identified markers may be used for the identification and isolation of one or more markers or genes from lettuce or other vegetable crops, particularly Asteraceae crops that are linked or encode *Bremia* resistance.

The invention is further described by the following non-limiting examples which further illustrate the invention, and are not intended to, nor should they be interpreted to, limit the scope of the invention.

Seeds resistant to *Bremia lactucae* races Bl:1 to Bl:28 generated by the schema shown in Example 2 below such that each seed is homozygous for the resistance locus were deposited with the National Collection of Industrial Food and Marine Bacteria (NCIMB), Craibstone Estate, Bucksburn, Aberdeen, AB219YA, UNITED KINGDOM, under Accession No. NCIMB 43449 on Jul. 31, 2019.

EXAMPLES

Example 1

Disease Test

The tests are done in a climate chamber with high humidity. Day length is 16 hours and during the day the temperature is 18° C. and RH about 85%. During the night the temperature is 15° C. and the RH round 100%. Before inoculation of a test the spores of the *Bremia* pathogen are multiplied on susceptible varieties. The choice of a susceptible variety for a *Bremia* isolate is made from the official differential host set and from an internal set. Disease testing for *Bremia* resistance was performed using all currently known *Bremia* strains or isolates (BI01-BI28). Performance of AS-002 was compared to currently known *Lactuca* varieties.

TABLE 1

|  | Green-Towers | Lednicky | UC DM2 | Dandie | R4T57D | Valmaine | Sabine | LSE 57/15 (BLaM) | UC DM10 | Capitan | Hilde II | Pennlake | UC DM14 | NunDm15 |
| --- | --- | --- | --- | --- | --- | --- | --- | --- | --- | --- | --- | --- | --- | --- |
| DM nr/R nr | 0 | 1 | 2 | 3 | 4 | 5/8 | 6 | 7 | 10 | 11 | 12 | 13 | 14 | 15 |
| Sextet nr |  | 1 | 2 | 3 | 4 | 5 | 6 | 7 | 8 | 9 | 10 | 11 | 12 | 13 |

TABLE 1-continued

| | | | | | | | | | | | | | | |
|---|---|---|---|---|---|---|---|---|---|---|---|---|---|---|
| Sextet value | | 1 | 2 | 4 | 8 | 16 | 32 | 1 | 2 | 4 | 8 | 16 | 32 | 1 |
| Bl:1 | + | + | + | − | + | − | − | − | + | − | + | + | + | − |
| Bl:2 − >CPVO | + | + | + | + | + | + | + | − | + | (−) | + | + | + | − |
| Bl:3 | + | − | − | − | + | + | + | + | + | − | + | + | (+) | + |
| Bl:4 | + | + | + | − | + | + | (−) | + | + | (−) | + | + | + | − |
| Bl:5 − >CPVO | + | + | − | + | − | − | − | + | + | − | + | + | − | + |
| Bl:6 | + | + | + | − | + | + | (−) | − | + | + | + | + | + | − |
| Bl:7 − >CPVO | + | + | + | + | + | − | + | + | + | − | + | + | + | (−) |
| Bl:10 | + | + | + | + | + | + | + | + | + | − | + | + | + | (−) |
| Bl:11 | + | + | − | − | + | + | + | + | + | − | + | + | + | + |
| Bl:12 − >CPVO | + | + | − | − | + | + | + | + | + | + | + | + | + | + |
| Bl:13 | + | + | − | + | − | + | (−) | + | + | + | + | + | + | − |
| Bl:14 − >CPVO | + | + | + | + | + | + | + | − | + | + | + | + | + | − |
| Bl:15 − >CPVO | + | + | + | + | + | + | − | + | + | + | + | + | − | − |
| Bl:16 − >CPVO* | + | + | + | + | + | + | + | + | + | + | + | + | − | − |
| Bl:17 *− >CPVO | + | − | + | + | − | + | − | + | + | − | + | + | + | + |
| Bl:18 *− >CPVO | + | + | + | − | + | + | + | + | + | + | + | + | − | − |
| Bl:19 | + | + | + | + | + | + | + | − | + | + | + | + | + | − |
| Bl:20 *− >CPVO | + | + | + | + | + | + | + | + | + | + | + | + | − | − |
| Bl:21 *− >CPVO | + | + | + | + | + | + | + | + | + | + | + | + | − | + |
| Bl:22 *− >CPVO | + | + | + | − | + | + | + | + | + | + | + | + | + | + |
| Bl:23 *− >CPVO | + | + | + | + | + | + | + | + | + | + | + | + | − | − |
| Bl:24 *− >CPVO | + | + | + | − | + | + | + | + | + | + | + | + | − | − |
| Bl:25 | + | + | + | − | + | + | + | + | + | + | + | + | − | − |
| Bl:26 | + | + | + | + | + | + | + | + | + | + | + | + | − | − |
| Bl:27 | + | + | + | + | + | + | + | + | + | + | + | + | + | + |
| Bl:28 | + | + | + | − | + | + | + | + | + | + | + | + | (−) | − |

| | CGDm 16 | NunDm17 | Colo-rado | Nin-ja | Dis-covery | Argeles | RYZ 2164 (Silvinas) | RYZ-line (Murai-res) | Bed-ford | Balesta | Bellis-simo | Jumbis | AS-002 |
|---|---|---|---|---|---|---|---|---|---|---|---|---|---|
| DM nr/R nr | 16 | 17 | 18 | 36 | 37 | 38 | | | | | | | |
| Sextet nr | 14 | 15 | 16 | 17 | 18 | 19 | 20 | 21 | 22 | 23 | 24 | | |
| Sextet value | 2 | 4 | 8 | 16 | 32 | 1 | 2 | 4 | 8 | 16 | 32 | | |
| Bl:1 | − | − | − | − | − | − | − | − | − | − | − | − | − |
| Bl:2 − >CPVO | − | − | (−) | − | − | + | − | − | − | + | + | − | − |
| Bl:3 | − | − | − | − | "+ | − | − | (−) | (−) | − | + | − | − |
| Bl:4 | (−) | − | (−) | − | − | − | − | − | − | (−) | − | − | − |
| Bl:5 − >CPVO | − | (−) | − | − | − | − | − | − | − | − | − | − | − |
| Bl:6 | (−) | − | − | − | − | − | − | (−) | − | − | − | − | − |
| Bl:7 − >CPVO | − | − | − | − | − | − | − | − | − | − | − | − | − |
| Bl:10 | − | − | − | − | − | − | − | − | − | − | − | − | − |
| Bl:11 | + | − | − | − | − | − | | | | | − | − | − |
| Bl:12 − >CPVO | + | − | − | − | − | − | − | − | − | − | − | − | − |
| Bl:13 | − | − | − | − | − | − | − | − | − | − | − | − | − |
| Bl:14 − >CPVO | − | − | − | − | − | − | − | − | − | − | − | − | − |
| Bl:15 − >CPVO | − | − | − | − | − | − | − | − | − | − | − | − | − |
| Bl:16 − >CPVO* | + | − | − | − | − | − | − | − | − | − | − | − | − |
| Bl:17 *− >CPVO | − | − | + | − | + | − | − | − | (+) | (−) | − | − | − |
| Bl:18 *− >CPVO | + | − | + | − | − | − | − | − | − | − | − | − | − |
| Bl:19 | − | − | − | − | − | + | − | − | (−) | (−) | − | − | − |
| Bl:20 *− >CPVO | + | − | + | − | − | − | − | − | − | − | (−) | − | − |
| Bl:21 *− >CPVO | + | − | − | + | + | − | − | (−) | (−) | − | − | − | − |
| Bl:22 *− >CPVO | − | − | + | − | − | (−) | − | − | (−) | + | − | − | − |
| Bl:23 *− >CPVO | + | − | − | − | − | + | − | − | − | − | − | − | − |
| Bl:24 *− >CPVO | + | − | + | − | − | + | − | − | − | − | − | − | − |
| Bl:25 | + | − | + | − | + | (−) | − | − | − | − | − | + | − |
| Bl:26 | + | − | + | + | + | + | − | − | − | − | − | + | − |
| Bl:27 | − | + | + | − | − | + | + | − | − | + | − | − | − |
| Bl:28 | + | − | + | − | − | + | − | + | − | − | (−) | − | − |

+: High level sporulation => susceptible (−): Brown necrotic spots without sporulation (+): Brown necrotic spots with sporulation −: No sporulation => resistance The set of 24 differential varieties consist of four groups of six varieties (sextets) (see Table 1). The position of a differential within the sextet determines the sextet value of that differential. Sextet values are ascending powers of 2 (1, 2, 4, 8, 16 or 32). The sextet code of an isolate is the sum of the sextet values of the differentials that are susceptible, as indicated by + or (+) in the table. For example, the first sextet code of Bl:27 is 63 because all differentials are susceptible and 1 + 2 + 4 + 8 + 16 + 32 = 63, and the fourth sextet code is 1 + 2 + 16 = 19. The virulence pattern of Bl:27 on the EU-B set is completely described by the codes of the four sextets as 63-63-13-19.

Example 2

Figure 1:
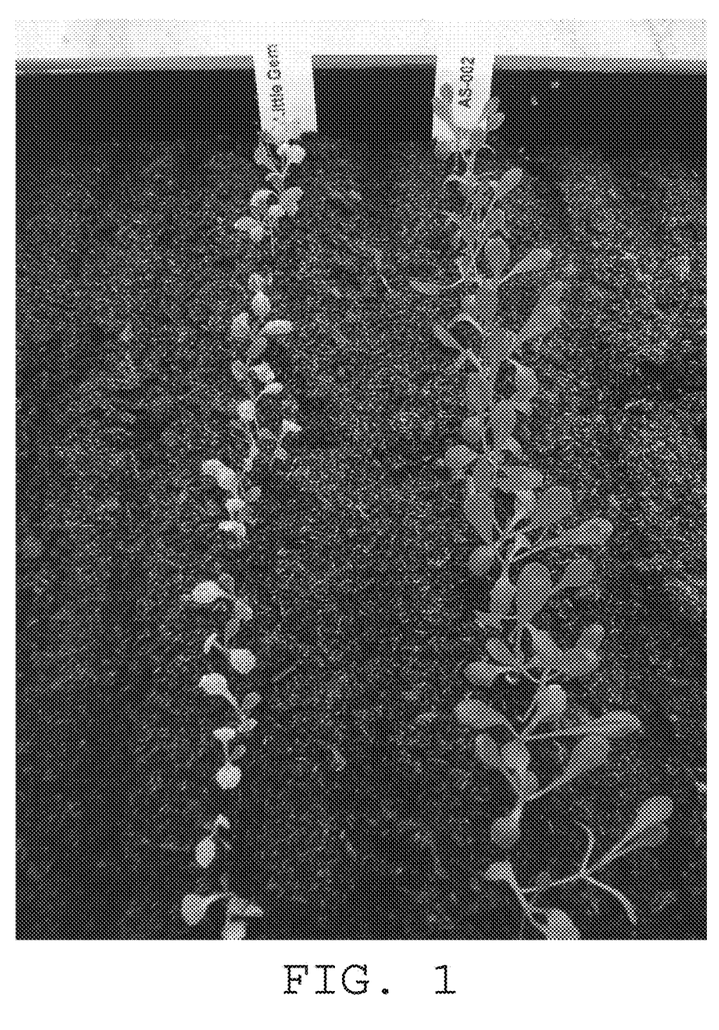
FIG. 1 shows a comparison between a plant according to the current invention and a regular plant. Both were inoculated with *Bremia lactucae*, only the plant according to the current invention showed resistance.
Figure 2:
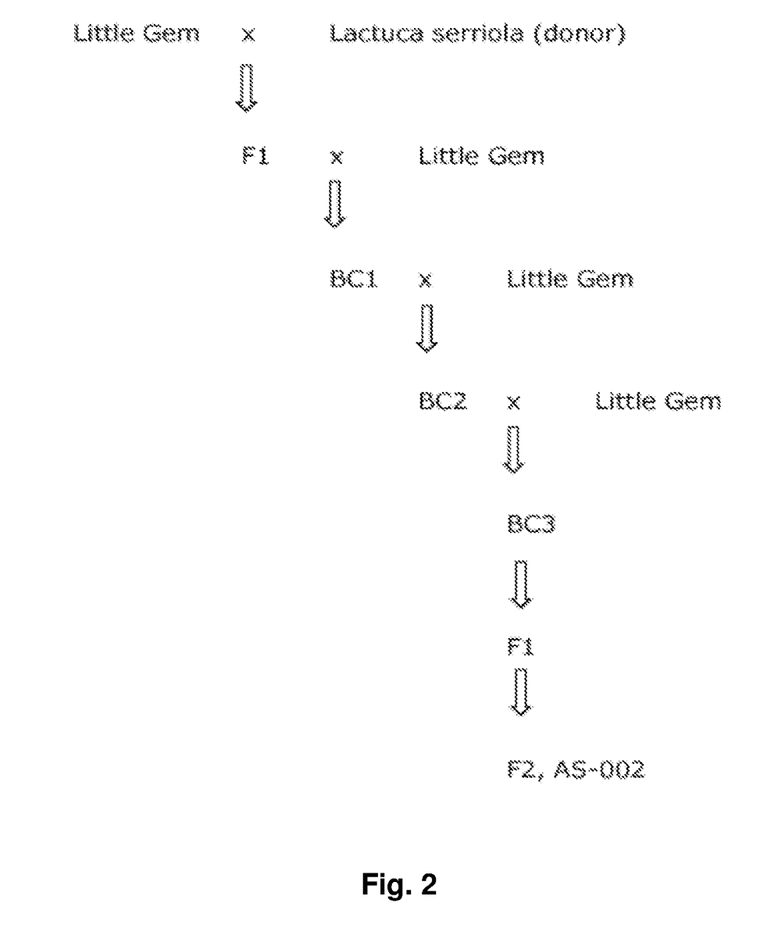
FIG. 2 shows a breeding scheme of a plant according to the current invention.

L. sativa plants according to the invention were obtained according to the scheme represented in FIG. 2 and described below.

A *Lactuca serriola* plant was crossed with *L. sativa* variety Little Gemwhich does not show *Bremia lactucae* resistance. F1 plants were tested for resistance to *Bremia lactucae* and a selected plant was backcrossed with a plant of the type "Little Gem". BC1 plants from this cross were checked for *Bremia* resistance and backcrossed with a plant of the type "Little Gem". BC3 progeny was further crossed and propagated until F2, which gave rise to a line which was uniform and segregated for resistance to *Bremia lactucae*.

Example 3

Two pools of DNA were generated; said one pool consisted of susceptible individuals (SUS) to the trait, whereas a second pool consisted of resistant individuals (RES) of the trait. Genomic DNA was isolated and pooled for Illumina HiSeq sequencing. Briefly the pooled gDNA was prepared for shot gun library preparation by strict fragmentation and end repair of gDNA, adapter ligation, size selection (approximately 300 bp) PCR amplification, library purification and Quality Control. Two flow channels were prepared and the two libraries were sequenced in Hiseq2500 2×150 bp paired-end mode. The data was collected and filtered according to Quality scores in Illumina pipeline 1.8.

The reference genome of *Lactuca sativa* was obtained from the *Lactuca* Genome Resources, built v4 Pseudomolecules. Both the RES data and the SUS data were stringently mapped against the Reference genome. The RES mapping file was used in Probablistic Variant Detection. The Variant data file was used to filter for variants that are also present in the SUS mapping file. As a consequence, variants were collected.

Subsequently, the variant control mapping file was inspected for Marginal Variants. Finally, two sequences, SEQ ID No. 1 or SEQ ID No. 2, were identified which are linked to the genetic determinant responsible for the resistance trait. The latter are located on linkage group 2.

These two marker sequences were separately used in a test on F2-material not included in the RES pool and were found consistent.

---

The invention claimed is:

1. A *Lactuca sativa* plant having resistance to *Bremia lactucae* races Bl:1 to Bl:28 and comprising in its genome SEQ ID No. 1 and SEQ ID No. 2, representative seed of said plant having been deposited under NCIMB Accession No. NCIMB 43449.

2. An F1 hybrid, or a first generation selfed progeny thereof, of the *Lactuca sativa* plant of claim 1, wherein said F1 hybrid or first generation selfed progeny thereof comprises in its genome SEQ ID No. 1 and SEQ ID No. 2.

3. A seed of the *Lactuca sativa* plant of claim 1, wherein said seed comprises in its genome SEQ ID No. 1 and SEQ ID No. 2.

4. A method for producing a *Lactuca sativa* plant having resistance to *Bremia lactucae* races Bl:1 to Bl:28, the method comprising:
   a. obtaining a first *Lactuca sativa* plant according to claim 1;
   b. crossing said first *Lactuca sativa* plant with a second *Lactuca sativa* plant to produce progeny seed; and
   c. growing said progeny seed to produce a third plant that comprises SEQ ID No. 1 and SEQ ID No. 2 and exhibits resistance to *Bremia lactucae* races Bl:1 to Bl:28.

5. A method for producing seed, the method comprising: crossing a first plant according to claim 1 with a second plant to produce seed, wherein said seed comprises SEQ ID No. 1 and SEQ ID No. 2, and wherein a plant grown from said seed exhibits resistance to *Bremia lactucae* races Bl:1 to Bl:28.

6. A plant part from the plant according to claim 1, wherein the plant part comprises SEQ ID No. 1 and SEQ ID No. 2.

7. The plant part of claim 6, wherein the plant part is at least one of a plant seed, a plant organ, a root, stem, leaf, flower bud, embryo, ovules, pollen microspores, plant cells, plant tissue, a cultured plant cell, protoplasts, cell culture cells, cells in plant tissues, microspores, pollen, pollen tubes, embryo sacs, and zygotes.

8. The plant part of claim 6, wherein the plant part is a head or one or more leaves.

9. The method of claim 4 further comprising: backcrossing said third plant with the first or second *Lactuca sativa* plant.

10. The method of claim 4 further comprising: d. crossing said third plant with a fourth plant to produce seed, wherein said seed comprises SEQ ID No. 1 and SEQ ID No. 2, and wherein a plant grown from said seed exhibits resistance to *Bremia lactucae* races Bl:1 to Bl:28.

11. A seed that produces the plant of claim 2.

12. A processed product from the plant of claim 1, wherein said product comprises SEQ ID No. 1 and SEQ ID No. 2.

13. A seed of a *Lactuca sativa* plant that is resistant to *Bremia lactucae* races Bl:1 to Bl:28 and includes in its genome SEQ ID No. 1 and SEQ ID No. 2, a sample of said seed having been deposited under NCIMB Accession No. NCIMB 43449.

14. A lettuce plant grown from the seed of claim 1.

15. A part of the lettuce plant of claim 14, wherein said part is a root, stem, leaf, flower bud, embryo, ovules, pollen microspore, plant cell, plant tissue, protoplast, cell culture cell, cell in plant tissue, microspore, pollen, pollen tube, ovule, embryo sac, or zygote.

16. A tissue culture of regenerable cells or protoplasts from the lettuce plant of claim 14.

17. A lettuce plant regenerated from the tissue culture of claim 16, wherein said plant comprises SEQ ID No. 1 and SEQ ID No. 2 and exhibits resistance to *Bremia lactucae* races Bl:1 to Bl:28.

* * * * *

SEQUENCE LISTING

<160> NUMBER OF SEQ ID NOS: 2

<210> SEQ ID NO 1
<211> LENGTH: 151
<212> TYPE: DNA
<213> ORGANISM: Lactuca

<400> SEQUENCE: 1

```
aggaggtaac tcgacgagtt gattcgactg ggagttaacc ttgactttga ctttgactag      60
gatgttcact ttaactaggg gtaaaatggt cattttaccc aaagatggat tatcagattt     120
taattaagtg ttattgtgaa attgatagtt g                                    151
```

<210> SEQ ID NO 2
<211> LENGTH: 151
<212> TYPE: DNA
<213> ORGANISM: Lactuca

<400> SEQUENCE: 2

```
tattggcatg ataaggtatc gtgacacatg tgctgaagcc atgcgtttct ttaaagaaaa      60
aggtcctact tttgccacga aatctgaagc ctgtagaaag atgcttgaag ttgattgtct     120
tgaagtgttg cctagcacag ttaagggaga t                                    151
```